United States Patent
Wachs et al.

(10) Patent No.: US 6,518,463 B2
(45) Date of Patent: Feb. 11, 2003

(54) METAL MOLYBDATE/IRON-MOLYBDATE DUAL CATALYST BED SYSTEM AND PROCESS USING THE SAME FOR METHANOL OXIDATION TO FORMALDEHYDE

(75) Inventors: Israel E. Wachs, Bridgewater, NJ (US); Laura Briand, Buenos Aires (AR)

(73) Assignee: Lehigh University, Bethlehem, PA (US)

( * ) Notice: Subject to any disclaimer, the term of this patent is extended or adjusted under 35 U.S.C. 154(b) by 0 days.

(21) Appl. No.: 09/950,834

(22) Filed: Sep. 13, 2001

(65) Prior Publication Data

US 2002/0062048 A1 May 23, 2002

Related U.S. Application Data

(60) Provisional application No. 60/232,628, filed on Sep. 14, 2000.

(51) Int. Cl.[7] .............................................. C07C 42/29
(52) U.S. Cl. ..................... 568/472; 568/473; 568/474
(58) Field of Search ................................ 568/472, 473, 568/474

(56) References Cited

U.S. PATENT DOCUMENTS

| | | | |
|---|---|---|---|
| 2,065,394 A | | 12/1936 | Punnett |
| 3,678,139 A | * | 7/1972 | McClellen et al. ... 260/603 HF |
| 3,716,497 A | | 2/1973 | Courty |
| 3,846,341 A | | 11/1974 | Courty |
| 3,975,302 A | | 8/1976 | Courty et al. |
| 3,983,073 A | | 9/1976 | Trifiro et al. |
| 3,987,107 A | | 10/1976 | McClellan et al. |
| 3,994,977 A | | 11/1976 | Aicher et al. |
| 4,024,074 A | | 5/1977 | Cairati et al. |
| 4,080,383 A | | 3/1978 | Diem et al. |
| 4,181,629 A | | 1/1980 | Cairati et al. |
| 4,343,954 A | | 8/1982 | Hoene |
| 4,421,938 A | | 12/1983 | Windawi |
| 4,584,412 A | | 4/1986 | Aicher et al. |
| 4,829,042 A | | 5/1989 | Cavalli et al. |
| 5,217,936 A | | 6/1993 | Sarup et al. |
| 6,245,708 B1 | | 6/2001 | Wachs et al. |

FOREIGN PATENT DOCUMENTS

| | | |
|---|---|---|
| EP | 0 199 359 | 10/1986 |
| GB | 1463174 | 2/1977 |
| WO | WO 98/23360 | 6/1998 |
| WO | WO 99/52629 | 10/1999 |
| WO | WO 99/52630 | 10/1999 |

OTHER PUBLICATIONS

G. Deo and I Wachs, *Journal of Catalysis*, 146, 335–345 (1994).

G. Deo and I Wachs, *Journal of Catalysis*, 146, 323–334 (1994).

* cited by examiner

*Primary Examiner*—Brian J. Davis
(74) *Attorney, Agent, or Firm*—Banner & Witcoff, Ltd.

(57) ABSTRACT

A process and fixed bed reactor for oxidizing methanol in a reactant gas feed stream to formaldehyde. The process comprises introducing the reactant gas feed stream into an upstream region containing a first metal molybdate catalyst (substantially free of a volatile $Mo/MoO_3$ species) under oxidizing conditions to form a partially oxidized reactant gas feed stream which is then introduced under oxidizing conditions into a downstream region containing a second metal molybdate catalyst to further oxidize any residual methanol contained therein. A fixed bed reactor comprising an upstream region and a downstream region containing the aforementioned first and second metal molybdate catalysts, respectively, is utilized to implement the inventive process to yield a product gas stream containing formaldehyde preferably at a conversion of 85% or more and a selectivity of 90% or more.

18 Claims, 2 Drawing Sheets

METAL MOLYBDATE/IRON-MOLYBDATE DUAL CATALYST BED SYSTEM AND PROCESS USING THE SAME FOR METHANOL OXIDATION TO FORMALDEHYDE

This application claims the benefit under 35 U.S.C. 119(e)(1) of prior filed provisional application 60/232,628, filed Sep. 14, 2000.

BACKGROUND OF THE INVENTION

1. Field of the Invention

The invention relates to a catalytic reactor bed arrangement comprising, in a specified distribution, a plurality of catalysts in one or more fixed bed reactors and a process using the same for conversion of methanol to formaldehyde. More particularly, the invention relates to (1) a catalytic reactor bed comprising, in a specified distribution, a first metal-molybdate catalyst and a second metal-molybdate catalyst, provided in one or more fixed bed reactors, and (2) a process using the same for oxidizing methanol to formaldehyde.

2. Description of the Related Art

The formation of formaldehyde involves the dehydrogenation and oxidation of methanol. One approach for converting methanol to formaldehyde involves oxidizing methanol over a silver catalyst. See, for example, U.S. Pat. Nos. 4,080,383; 3,994,977; 3,987,107; 4,584,412; 4,343,954 and 4,343,954. Typically, methanol oxidation to formaldehyde over a silver catalyst is carried out in an oxygen lean environment. One problem associated with silver catalyzed methanol oxidation is methanol leakage i.e., high amounts of unconverted methanol.

Accordingly, improved processes for oxidizing methanol to formaldehyde have been developed. These processes use a methanol/air mixture (e.g., a reactant gas feed stream of methanol, excess air and an inert carrier gas) introduced over an iron-molybdate/molybdenum trioxide catalyst. See, for example, U.S. Pat. Nos. 3,983,073 (conversion of methanol to formaldehyde using $Fe_2(MoO_4)_3$ and $MoO_3$ having a molar ratio of Mo/Fe from 1.5 to 1.7 and a degree of crystallinity of at least 90%); 3,978,136 (process for the conversion of methanol to formaldehyde with a $MoO_3$/$Fe_2O_3$/$TiO_2$ catalyst wherein the $MoO_3$:$Fe_2O_3$ weight ratio is between 1:1 to 10:1 and $TiO_2$ is present between 1 to 90 weight % of total oxides); 3,975,302 (a supported iron oxide and molybdenum trioxide catalyst wherein the atomic ratio of Mo/Fe is from 1.5 to 5); 3,846,341 (a shaped and optionally supported iron molybdate type catalyst having high mechanical strength made by reacting ammonium molybdate and ferric molybdate); 3,716,497 (an optionally shaped iron molybdate type catalyst made by admixing with $NH_4^+A^-$); 4,829,042 (high mechanical strength catalyst of $Fe_2(MoO_4)_3$ and $MoO_3$ together with non-sintered $Fe_2O_3$); 4,024,074 (interaction product of $Fe_2(MoO_4)_3$, $MoO_3$ and bismuth oxide for catalyzing oxidation of methanol to formaldehyde); 4,181,629 (supported catalyst of iron oxide and molybdenum oxide on silica, alumina and the like); 4,421,938 (a supported catalyst of at least two oxides of Mo, Ni, Fe and the like); and 5,217,936 (a catalyst of a monolithic, inert carrier and oxides of molybdenum, iron and the like).

In comparison to the silver catalyzed processes, iron-molybdate/molybdenum trioxide catalyzed processes produce higher yields of formaldehyde. Iron-molybdate, $Fe_2(MoO_4)_3$, in combination with molybdenum trioxide, $MoO_3$, constitute the metal oxide phases of exemplary commercially available metal oxide catalysts suitable for oxidizing methanol to formaldehyde. During the oxidation of methanol to formaldehyde, the $Fe_2(MoO_4)_3MoO_3$ catalyst can be generated in situ from physical mixtures of pure molybdenum trioxide, $MoO_3$, and ferric oxide, $Fe_2O_3$. See copending patent application designated by attorney docket no. 00242.72876 and Provisional Application No. 60/081,950 entitled "In Situ Formation of Metal Molybdate Catalysts" of Wachs et al., filed on Apr. 15, 1998. The molar ratio $MoO_3$/$Fe_2O_3$ of these catalysts may be varied. Typically, such catalysts used in industrial and commercial applications contain an excess of $MoO_3$. Thus, for example, the molar ratio $MoO_3$/$Fe_2O_3$ may vary from 1.5/1 to 12/1 or more. Excess $MoO_3$ is provided to ensure that sufficient amounts of $Fe_2(MoO_4)_3$ are formed in situ (from the mixture of $Fe_2O_3$ and $MoO_3$) for efficiently oxidizing methanol to formaldehyde in high yields.

Unfortunately, the use of excess $MoO_3$ in conjunction with $Fe_2O_3$ or other metal oxides and/or metal molybdates is problematic. Oxidizing methanol to formaldehyde using a metal molybdate/molybdenum trioxide type catalyst, e.g., $Fe_2(MoO4)_3$/$MoO_3$, is a highly exothermic process. The heat released during the oxidation reaction increases the catalyst and/or the fixed bed reactor temperature producing "hot spots" on the catalyst surface. These hot spots reach temperatures high enough to volatilize the $Mo$/$MoO_3$ species present within metal molybdate/molybdenum trioxide type catalysts. Thus, $Mo$/$MoO_3$ is sublimed from the hot spots so formed.

The sublimed $Mo$/$MoO_3$ species migrate downstream (e.g., within an exemplary fixed bed reactor housing the catalyst) towards cooler regions of the fixed bed reactor or the like. Typically, the downstream migration of sublimed $Mo$/$MoO_3$ species is facilitated by the incoming flow of the reactant gas feed stream containing, for example, methanol, air, and an optional inert carrier gas fed into the inlet end of a fixed bed reactor. The migrated $Mo$/$MoO_3$ species crystallize in the cooler downstream regions of the fixed bed reactor, for example, in the form of $MoO_3$ crystalline needles. Over time, the needle formation accumulates and ultimately obstructs the flow of the reactant gas feed stream through the fixed bed reactor. Thus, build up of $MoO_3$ crystals/needles in the downstream region causes a substantial pressure drop in the reactant gas feed stream flow rate as the reactant gas feed stream is directed downstream. This pressure drop impedes the efficient oxidation of methanol to formaldehyde. See, for example, U.S. Pat. Nos. 3,983,073 (col. 1, lines 35–52); and 4,024,074 (col. 1, lines 60–68); and U.K. Patent No. 1,463,174 (page 1, col. 2, lines 49–59) describing the aforementioned volatility problem.

Often, the $MoO_3$ needle formation that occurs in the downstream region of the fixed bed reactor is so excessive that the reactor must be shut down, the needles cleaned out, and fresh catalyst charged therein. These steps unnecessarily increase the time, cost, inefficiency and/or complexity of operating a fixed bed reactor or the like for oxidizing methanol to formaldehyde.

Accordingly, there is a need to provide a catalytic reactor bed arrangement comprising, in a specified distribution, a plurality of catalysts within one or more fixed bed reactors and a process using the same that substantially alleviates, and/or eliminates the aforementioned crystallization problems associated with metal molybdate catalysts containing volatile $Mo$/$MoO_3$ species.

Further, (1) silver catalysts, (2) supported catalysts such as those containing silicon dioxide, titanium dioxide, non-sintered $Fe_2O_3$, bismuth interaction products, silica, and/or alumina, (3) high surface area solid supported catalysts, (4) catalysts containing zinc, zinc carbonates and/or indium, (5) catalysts on inert carriers of fibrous carrier material such as fibrous sheets of silica or monolithic inert carriers, (6) shaped catalysts, and (7) the like are often prohibitively expensive to use. Accordingly, there remains a need for a catalytic bed reactor arrangement (containing a specified distribution of a plurality of methanol oxidation catalysts) and a method using the same suitable for cost effectively oxidizing methanol to formaldehyde which is free or substantially free of one or more of (1) silicon dioxide, (2) titanium dioxide, (3) non-sintered $Fe_2O_3$, (4) interaction products of $Fe_2(MoO_4)_3$, and $MoO_3$, and bismuth, (5) silica, (6) alumina, (7) supported catalysts, (8) shaped catalysts for increasing mechanical strength, (9) catalysts containing $Zn(CO_3)$. $3Zn(OH)_{,2}$ $In(NO_3)_3$. $3H_2O$ or one or more of the compounds listed in U.S. Pat. No. 4,421,938, (10) a fibrous carrier material such as silica, (11) monolithic inert materials or (12) the like.

SUMMARY OF THE INVENTION

It is therefore an object of the invention to provide a catalytic reactor bed arrangement of two or more catalysts, in a specified distribution, within one or more fixed bed reactors and a process using the same for converting methanol to formaldehyde that alleviates and/or eliminates one or more of the above mentioned problems associated with the volatility of $Mo/MoO_3$.

It has been surprisingly discovered that use of a substantially pure metal molybdate catalyst (e.g., essentially free of volatile $Mo/MoO_3$ species) distributed in an upstream region of one or more fixed bed reactors together with a conventional type catalyst within the downstream region of the fixed bed reactor provides a high selectivity (e.g., nearly 90–100%) and/or high conversion % (e.g., at least 85–95%) for oxidizing methanol to formaldehyde while eliminating and/or substantially alleviating the above mentioned volatility problems associated with $Mo/MoO_3$.

According to one aspect of the invention, oxidation of methanol to formaldehyde is achieved by the exemplary process described below. The process comprises the steps of:

(a) providing at least one fixed bed reactor having an inlet end, an upstream region, a downstream region, and an outlet end, wherein the fixed bed reactor comprises a catalytic reactor bed comprising a first metal molybdate catalyst in the upstream region and a second metal molybdate catalyst in the downstream region, and wherein the upstream region is essentially free of a volatile $Mo/MoO_3$ species;

(b) introducing a reactant gas feed stream comprising methanol into the inlet end; and (c) contacting and oxidizing the methanol to formaldehyde with the fist metal molybdate catalyst to yield a partially oxidized reactant gas feed stream potentially containing residual methanol; and (d) then contacting and oxidizing the residual methanol to formaldehyde with the second metal molybdate catalyst to yield a product gas stream.

According to another aspect of the invention, an exemplary catalytic reactor bed comprises a first metal molybdate catalyst in an upstream region and a second metal molybdate catalyst in a downstream region of the fixed bed reactor, respectively. The first metal molybdate catalyst must be essentially free of a volatile species of $Mo/MoO_3$ sufficient to alleviate and/or eliminate a substantial pressure drop of the reactant gas feed stream (comprising methanol) as it flows through the fixed bed reactor.

DETAILED DESCRIPTION OF THE PREFERRED EMBODIMENTS

Oxidizing methanol to formaldehyde may be facilitated by the use of two or more catalysts having a specified distribution within a fixed bed reactor. Typically, the fixed bed reactor has an inlet end, an upstream region, a downstream region and an outlet end. Preferably, the inlet end, the upstream region, the downstream region and the outlet end are provided in the same order as indicated herein. For example, see FIGS. 2 and 3. The catalysts are distributed as described in greater detail below with reference to the exemplary fixed bed reactors depicted in FIGS. 2 and 3. These fixed bed reactors are suitable for carrying out the process of the invention including the exemplary process steps outlined FIG. 1.

Figure 1:
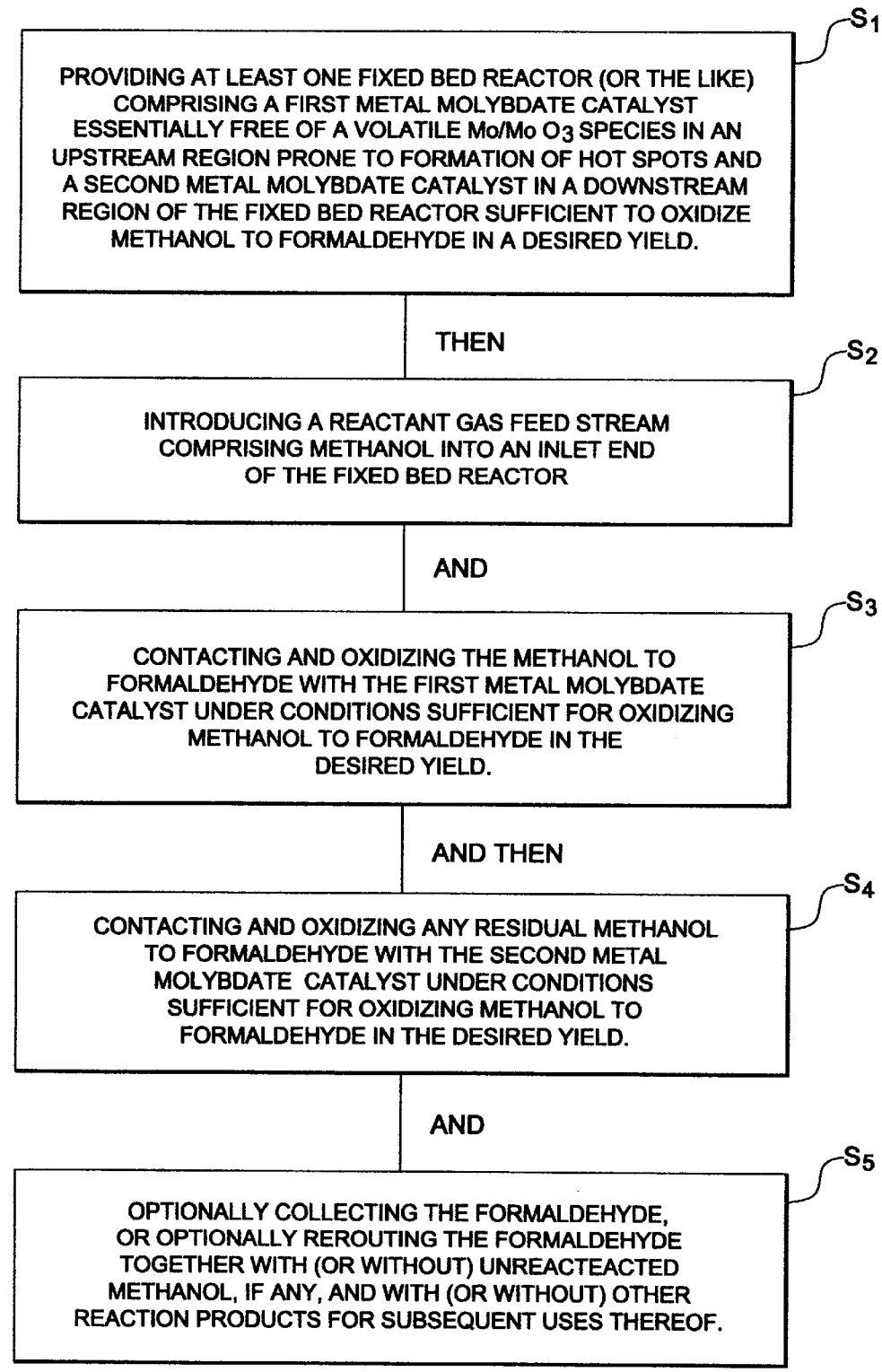
FIG. 1 is a flow chart depicting the process of this invention according to one embodiment.

Now referring to FIG. 1, process step $S_1$ comprises providing at least one fixed bed reactor (or the like). The fixed bed reactor includes a catalytic reactor bed (i.e., the upstream and downstream regions of the fixed bed reactor) comprising a plurality of catalysts in a specified distribution. The specified distribution comprises providing a first metal molybdate catalyst (essentially free of a volatile $Mo/MoO_3$ species) in the upstream region of the fixed bed reactor and a second metal molybdate catalyst in the downstream region of the fixed bed reactor. For the reasons previously described, the upstream region of the fixed bed reactor is the region prone to substantial formation of hot spots during the catalytic oxidation of methanol to formaldehyde.

Figure 2:
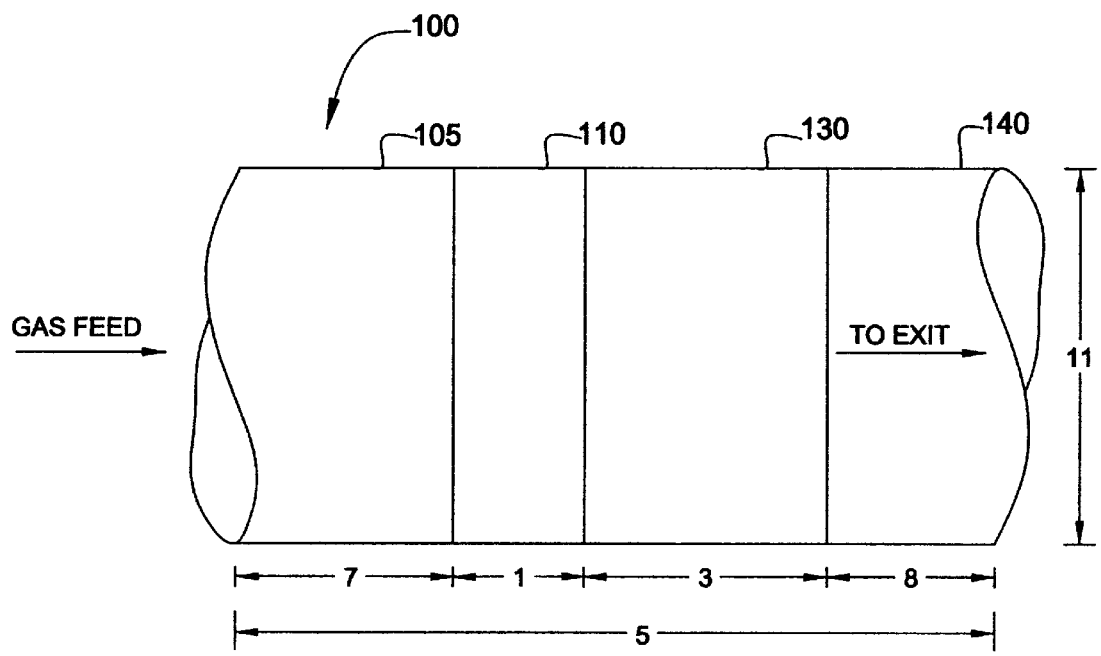
FIG. 2 is a schematic of a tubular fixed bed reactor according to one embodiment of the invention.
Figure 3:
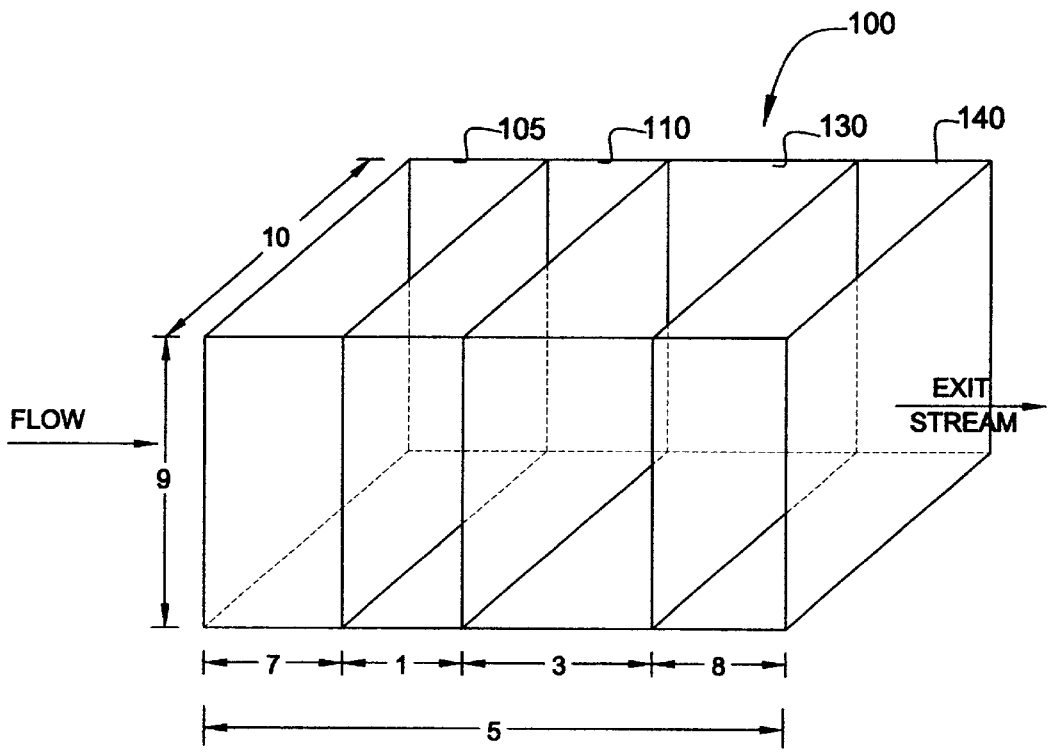
FIG. 3 is a schematic of a block fixed bed reactor according to another embodiment of the invention.

With reference to FIGS. 2 and 3, typically, the upstream region 110 of depth 1 comprises from about 1/8 to about 7/8 of the total depth 5 of the fixed bed reactor. Preferably, the upstream region comprises from about 3/8 to about 7/8 of the total depth 5 of the fixed bed reactor, more preferably from about 1/2 to about 7/8 of the total depth 5 of the fixed bed reactor, and even more preferably from about 5/8 to about 3/4 of the total depth 5 of the fixed bed reactor.

Further, with reference FIG. 1, process step $S_1$ comprises providing a second metal molybdate catalyst in the downstream region of the fixed bed reactor. The downstream region of the fixed bed reactor is substantially less prone to formation of hot spots than the upstream region because substantial conversion of methanol to formaldehyde (as described below) has already occurred in the upstream region of the fixed bed reactor. Accordingly, only residual methanol (yet unconverted to formaldehyde) is oxidized to formaldehyde in the downstream region. Typically, because the amount of the residual methanol is substantially less than the amount of the methanol in the reactant gas feed stream entering the upstream region, formation of hot spots is substantially suppressed in the downstream region. Accordingly, a conventional metal molybdate type catalyst (e.g., $Fe_2(MoO_4)_3$ together with excess $MoO_3$) may be and preferably is provided in the downstream region. As previously noted, because hot spot formation is suppressed in the downstream region, the volatility/crystallization/pressure drop problems associated with the use of volatile $MoO_3$ components in an upstream region are substantially attenuated or altogether avoided in the downstream region.

With reference to FIGS. 2 and 3, typically, the downstream region 130 of depth 3 comprises from about 1/8 to about 3/4 of the total depth 5 of the fixed bed reactor. Preferably, the downstream region comprises from about 1/8 to about 5/8 of the total depth 5 of the fixed bed reactor, more preferably from about 1/8 to about 1/2 of the total depth 5 of the fixed bed reactor, and even more preferably from about 3/8 to about 1/4 of the total depth 5 of the fixed bed reactor.

The first metal molybdate catalyst and the second metal molybdate catalyst provided in the specified distribution (e.g., step $S_1$ of FIG. 1) in a fixed bed reactor (i.e., in the catalytic reactor bed comprising the upstream region and the downstream region) are provided in amounts, particle sizes, having surface areas and the like sufficient to oxidize an incoming reactant feed gas stream introduced into an inlet end (e.g., inlet end 105 of depth 7; see FIGS. 2 and 3) to yield a product gas stream at the outlet end (e.g. outlet end 140 of depth 8; see FIGS. 2 and 3) containing formaldehyde in a desired yield.

Referring now to step $S_2$ of FIG. 1, a reactant gas feed stream comprising methanol is introduced into an inlet end (e.g., inlet end 105 of depth 7; see FIGS. 2 and 3) of the fixed bed reactor. The depth 7 of the inlet end may be from about $\frac{1}{1000}$ to about $\frac{1}{10}$ the overall depth 5 of the fixed bed reactor. Alternatively, the inlet end 105 may not have any substantial or appreciable depth 7. In that case, inlet end 105 simply refers to an opening for receiving an incoming reactant gas feed stream. Typically, the reactant gas feed stream comprises methanol, air or excess oxygen, and optionally an inert carrier gas (e.g., $N_2$, He, or the like). The reactant gas feed stream enters the inlet end 105 and travels towards the outlet end 140.

As the reactant gas feed stream approaches the upstream region, the reactant gas feed stream encounters and comes in contact with the first metal molybdate catalyst distributed in the upstream region 110 of the fixed bed reactor. Accordingly, (part of step $S_2$ of FIG. 1) contacting the reactant gas feed stream with the first metal molybdate catalyst is accomplished. The flow rate of the incoming gas feed stream, its temperature, its humidity, and other parameters are adjusted to those suited to oxidizing methanol to formaldehyde. These details are well known to those of ordinary skill in the art. However, some preferred operating parameters are provided in greater detail below.

The flow rate (e.g., in terms of space velocity=((sccm of gas flow)/(cc of catalyst volume)×(1 min/60 sec))) of the reactant gas feed stream fed into the inlet end of an exemplary fixed bed reactor ranges from about 0.1 $\sec^{-1}$ to about 3.0 $\sec^{-1}$, preferably ranges from about 0.3 $\sec^{-1}$ to about 2.5 $\sec^{-1}$, more preferably ranges from about 0.4 $\sec^{-1}$ to about 2.2 $\sec^{-1}$ and even more preferably ranges from about 0.5 $\sec^{-1}$ to about 1.5 $\sec^{-1}$ The reactor temperature in the upstream region of an exemplary fixed bed reactor typically ranges from about 300° C. to about 450° C., preferably ranges from about 325° C. to about 425° C., more preferably ranges from about 350° C. to about 400° C., and even more preferably ranges from about 360° C. to about 380° C.

Upon passage of the reactant gas feed stream through the upstream region, a significant portion of the methanol content thereof is converted to formaldehyde. However, some residual (yet unoxidized) methanol may be present within the partially oxidized reactant gas feed stream. At this stage through the fixed bed reactor, the reactant gas feed stream typically also contains residual methanol, air, an inert carrier gas (if initially provided) and other oxidation products well known to those skilled in the art. However, because the upstream region of the fixed bed catalyst is essentially free of a volatile $Mo/MoO_3$ species, the highly exothermic nature of the methanol oxidation reaction yielding formaldehyde (in the upstream region) avoids the aforementioned volatility/sublimation/pressure drop problems associated with the presence of volatile $Mo/MoO_3$ species (i.e., in an upstream region prone to hot spot formation). As it passes through and exits the upstream region, the reactant gas feed stream is partially oxidized typically containing significant quantities of formaldehyde.

Upon exit from the upstream region 110, the partially oxidized reactant gas feed stream typically containing formaldehyde, and residual methanol (together with other components) encounters and comes in contact with the second metal molybdate catalyst provided in the downstream region 130 of depth 3. Therein, a conventional second metal molybdate catalyst is provided to oxidize the residual methanol (that may potentially be present in the partially oxidized reactant gas feed stream), thereby, potentially improving the formaldehyde yield.

The reactor temperature of the downstream region of an exemplary fixed bed reactor typically ranges from about 300° C. to about 450° C., preferably ranges from about 305° C. to about 425° C., more preferably ranges from about 310° C. to about 400° C., and even more preferably ranges from about 320° C. to about 350° C.

Typically, upon passage through the downstream region, the partially oxidized reactant feed gas stream is now essentially fully oxidized and the reactant gas feed stream is hereafter referred to as the product gas stream. Formaldehyde is a significant component of the product gas stream together with quantities of one or more of air, some unreacted methanol (if any), water vapor or condensed water in aerosol form or the like, an inert carrier gas (if any), oxygen, and other products such as DMM (dimethoxy methane), DME (dimethyl ether), CO, $CO_2$ and the like.

As the reactant Was feed stream completes passage and oxidation through the upstream and downstream regions, process steps $S_3$ and $S_4$ (i.e., contacting the first and second metal molybdate catalysts and oxidizing methanol to formaldehyde; see FIG. 1) are essentially completed. The product gas stream then exits the outlet end 140 of depth 8. The outlet end 140 has a depth 8 which is from about $\frac{1}{1000}$ to about $\frac{1}{10}$ the overall depth 5 of the fixed bed reactor. Often, the outlet end 140 may not have any substantial or appreciable depth 8. In that case, outlet end 140 simply refers to an opening for releasing the product gas stream.

Optionally, thereafter, the product gas stream may be recycled into any one of the upstream region, or the downstream region as desired for further oxidation. However, if the product gas stream is to be recycled into the upstream region and possibly comingled with a fresh supply of an incoming reactant feed gas stream, it may be preferable (1) to first remove formaldehyde from the product gas stream by conventional means such as distillation, condensation and the like or (2) to substantially dilute the product gas stream to minimize the possible further oxidation of formaldehyde (in the upstream region) to its undesirable oxidation products such as CO, $CO_2$ or the like. Additionally, the product gas stream may be routed to another process that utilizes the product gas stream in its state as it exits the outlet end 140. Alternatively, the formaldehyde in the product gas stream may be collected by methods known to those of ordinary skill including distillation, condensation or the like.

The fixed bed reactors illustrated in FIGS. 2 and 3 have an inlet end 105 of depth 7, an upstream region 110 of depth 1, a downstream region 130 of depth 3, and an outlet end 140 of depth 8 . Each of depths 1, 3, 7 and 8 may be adjusted to a value sufficient to facilitate oxidizing methanol to formaldehyde in the desired conversion and the desired selectivity.

Further, the exemplary fixed bed reactor of FIG. 2 has a diameter 11 and the fixed bed reactor of FIG. 3 has a height 9 and a width 10. Each of the dimensions corresponding to reference numerals 9, 10 , and 11 may be adjusted upwards or downwards as necessary to accommodate the desired reactor size, the desired operating conditions, the desired conversion and selectivity.

As used herein, the term "selectivity" is determined by dividing the number of moles of formaldehyde formed by the number of moles of methanol consumed from the reactant gas feed stream times 100. Accordingly, selectivity is a percentage value Selectivity indicates the percentage of formaldehyde formed as compared to the percentage of non-formaldehyde oxidation products of methanol such as $CO$, $CO_2$, DMM, DME, etc. As used herein, the term "conversion" is determined by dividing the difference between the number of moles of methanol fed to the fixed bed reactor in the reactant gas feed stream minus the number of moles of methanol exiting the reactor by the total number of moles of methanol fed times 100. Accordingly, conversion is a percentage value. Conversion indicates the percentage of the moles of methanol that were oxidized to formaldehyde and any other non-formaldehyde oxidation products of methanol. Thus, if 2 moles of methanol are fed into the fixed bed reactor (e.g., in a reactant gas feed stream) yielding 1 mole of formaldehyde and 1 mole of methanol, then selectivity would equal 100% while conversion would equal 50%. Likewise, if 3 moles of methanol are fed into the fixed bed reactor (e.g., in a reactant gas feed stream) yielding 2 moles of formaldehyde and 1 mole of methanol, then selectivity would equal 100% while conversion would equal 66 and ⅔%.

Further, the fixed bed reactors are operated at an appropriate reactor temperature, a reactor pressure and a reactant gas feed stream flow rate sufficient for oxidizing methanol to formaldehyde in the desired yield, conversion and/or selectivity. Suitable exemplary reactor temperatures range from about 300° C. to about 450° C. Suitable exemplary reactor pressures range from about 7 psia (i.e., about ½ atm) to about 165 psia. Suitable exemplary reactant gas space velocity ranges from 0.5 $sec^{-1}$ to about 3.0 $sec^{-1}$. Other conditions suitable for oxidizing methanol to formaldehyde are used which are well known to those of ordinary skill in the art.

According to one embodiment of the invention, a first metal molybdate catalyst substantially free of a volatile $Mo/MoO_3$ species is distributed within the upstream region 110 of a fixed bed reactor 100, Metal molybdates suitable for use in the upstream region of the fixed bed reactor are (1) those that are stable in the hot spots formed in the fixed bed reactor during methanol oxidation to formaldehyde and (2) those catalysts that do not yield substantial quantities of a volatile $Mo/MoO_3$ species for deposition as crystals in the downstream region of the fixed bed reactor or in any other region of the fixed bed reactor in quantities sufficient to cause a substantial pressure drop of the reactant gas feed stream flowing through the fixed bed reactor. Typically, the mole ratio of the Mo to the metal (of the first metal molybdate catalyst in the upstream region) is from about 1:1 to about 1.5:1 (e.g., 1:1≦mole ratio≦1.1, 1.2, 1.3, 1.4, or 1.5, respectively), and, more typically, about 1.1:1. Use of suitable metal molybdate catalysts in the upstream region of a fixed bed reactor avoids and/or alleviates the problematic volatilization of $Mo/MoO_3$ species previously described. Thus, pressure drops of the reactant gas feed stream through the fixed bed reactor are substantially avoided and/or attenuated.

Preferably, the first metal molybdate catalyst is $NiMoO_4$ which is substantially free of a volatile $Mo/MoO_3$ species. Other first metal molybdate catalysts suitable for use with the invention, include but are not limited to, one or more molybdates of group IIIA (e.g., Al), molybdates of group IIB (e.g., Zn), molybdates of group IVB (e.g., Zr), molybdates of group VIB (e.g., Cr), and molybdates of group VIIB (e.g., Mn), respectively. For example, molybdates such as $MnMoO_4$, $Cr_2(MoO_4)_3$, $ZnMoO_4$, $Al_2(MoO_4)_3$, $Zr(MoO_4)_2$ or mixture thereof may be used as the first metal molybdate catalyst distributed in the upstream region. In addition, group VIII metal molybdate catalysts such as $CoMoO_4$ may be used as a first metal molybdate catalyst in the upstream region of the fixed bed reactor of the invention. Typically, stable molybdates substantially free of a volatile $Mo/MoO_3$ species may be distributed within the upstream region of a fixed bed reactor. However, $NiMoO_4$ is preferred.

The first metal molybdate typically has a surface area ranging from about 1.0 $m^2/g$ to about 20 $m^2/g$, preferably ranging from about 2 $m^2/g$ to about 18 $m^2/g$, more preferably ranging from about 2 $m^2/g$ to about 15 $m^2/g$, and even more preferably ranging from about 4 $m^2/g$ to about 12 $m^2/g$.

Because the downstream region 130 is not as prone to formation of hot spots as is the upstream region 120, it is preferable and less expensive to use a conventional metal molybdate catalyst in the downstream region 130. Examples of second metal molybdate catalysts suitable for use with the invention include, but are not limited to $Fe_2(MoO_4)_3$, $Fe_2(MoO_4)_3/MoO_3$, other group VIII metal molybdate catalysts (e.g., molybdates of Fe, Co, Ni, Cr AL, Zr, Zn, Mn or mixtures hereof). The group VIII metal molybdate catalysts may contain $Mo/MoO_3$ in minor or larger quantities. Preferably, the second metal molybdate catalyst is a metal molybdate/molybdenum trioxide catalyst such as $Fe_2(MoO_4)_3/MoO_3$. The $Fe_2(MoO_4)_3/MoO_3$ catalyst may be formed in situ during the oxidation of methanol to formaldehyde from a mixture of substantially pure $Fe_2O_3$ and $MoO_3$ wherein an excess of $MoO_3$ is typically provided. See copending application designated by Provisional Application No. 60/081,950 entitled "In Situ Formation of Metal Molybdate Catalysts" of Wachs et al., filed Apr. 15, 1998, incorporated herein by reference in its entirety. Alternatively, the second metal molybdate/molybdenum oxide catalyst may be $NiMoO_4/MoO_3$ wherein an excess of MoO is provided. The $NiMoO_4/MoO_3$ catalyst may be formed in situ (during the oxidation of methanol to formaldehyde) from a mixture of substantially pure NiO and an excess of $MoO_3$.

The second metal molybdate typically has a surface area ranging from about 0.5 $m^2/g$ to about 20 $m^2/g$, preferably ranging from about 2 $m^2/g$ to about 15 $m^2/g$, more preferably ranging from about 4 $m^2/g$ to about 14 $m^2/g$, and even more preferably ranging from about 4 $m^2/g$ to about 12 $m^2/g$. Further, the weight ratio (first metal molybdate catalyst/second metal molybdate catalyst) typically ranges from about 0.1 to about 10, preferably ranges from about 0.5 to about 8, more preferably ranges from about 1 to about 6, and even more preferably ranges from 2 to about 5.

Having described the invention, the following illustrative examples are provided. These examples are illustrative of preferred aspects of the invention and are not intended to limit the scope of the invention. All patents, publications and any other references cited herein are incorporated by reference herein in their entirety, respectively. In that regard, related provisional applications (1) "Dual Catalyst Bed Reactor for Methanol Oxidation" filed on even date and (2) "Vanadia-Titania/Metal-Molybdate Dual Catalyst Bed System and Process Using the Same for Methanol Oxidation to Formaldehyde" filed on even date are incorporated by reference herein in their entirety.

EXAMPLES

A comparison of the performance of various catalysts for oxidizing methanol to formaldehyde is provided in greater detail below.

A mixture of helium and oxygen from two mass flow controllers (Brooks) were bubbled through a methanol saturator cooled by flowing water from a cooler (Neslab RTE 110) to obtain a 6/16/78 ($CH_3OH/O_2/He$ mole %; totaling 100 mole %) mixture of methanol/oxygen/helium and a flow rate of ~100 standard cubic centimeter per minute (sccm). The reactor was held vertical and made of a suitable outer diameter (e.g., ≦6-mm, adjusted as necessary to hold the volume and weight of the catalyst(s) being used in the upstream and downstream regions of the catalyst bed) Pyrex glass. The catalysts (first metal-molybdate cyst in the upstream region and second metal-molybdate catalyst in the downstream region) were held at the middle of the Pyrex tube. The outlet of the reactor to the gas chromatograph (GC) was heated at 393–403° K (or as necessary) in order to avoid condensation of the products. The products were analyzed by a GC (HP5840) equipped with two TCDs (Thermal Conductive Detector) and a FID (Flame Ionization Detector), and two columns (Poropak R and Carbosieve SII) connected in parallel. Blank runs were performed on the Pyrex tube packed with quartz wool without any detectable conversions. See, G. Deo and I. Wachs, *J. Canal.* 146, 323–334 (1994); and G. Deo and I. Wachs, *J. Catal.* 146, 335–345 (1994).

Comparative Example 1

TABLE 1

| Catalyst Used | Surface Area ($S_{BET}$) in $m^2/g$ | $N_s$ in ($\mu mol/g$) | Reaction Rate in ($\mu mol/g \cdot sec$) | TOF at 300° C. in ($sec^{-1}$) | Selectivity in (%) to HCHO |
|---|---|---|---|---|---|
| $NiMoO_4$ | 9.5 | 19.00 | 3.00 | 0.16 | 100 |
| $NiMoO_4 + MoO_3$ (Mo/Ni mole ratio 2.2) | n/a | 8.26 | 9.21 | 0.93 | 83.3 |
| $Fe_2(MoO_4)_3$ | 9.6 | 52.00 | 11.17 | 0.14 | 61.0 |
| $Fe_2(MoO_4)_3 + MoO_3$ (Mo/Fe mole ratio 2.2) | 3.5 | 19.00 | 38.60 | 1.79 | 85.3 |
| $Fe_2O_3 + MoO_3$ (Mo/Fe mole ratio 2.2) | 21.4($Fe_2O_3$) | 11.0 (fresh cat.) | 21.0 | 1.76 | 88.2 |
| $NiO + MoO_3$ (Mo/Ni mole ratio 2.2) | 34.4(NiO) | 25.8 (fresh cat.) | 16.0 | 0.51 | 80.9 |

The catalytic activity of the pure molybdates were obtained at 380° C. and extrapolated to 300° C.
$N_s$ = number of active sites = $\mu$moles of $CH_3OH$ chemisorbed per gram of catalyst
TOF = Turnover Frequency )$sec^{-1}$) = number of $CH_3OH$ molecules converted per acitve site per second.

Comparative Example 2

The data presented in Table 2 below compares the various conversions and selectivities for oxidizing methanol with 100 mg of sample at 380° C.

TABLE 2

| Catalyst | HCHO, % | DME, % | others | Conversion, % |
|---|---|---|---|---|
| Perstorp Commercial Catalyst ($Fe_2(MoO_4)_3/MoO_3$) | 85.9 | 1.1 | CO, unknown | 100 |
| $Fe_2O_3/MoO_3$ (Mo/Fe molar ratio = 2.2) | 84.3 | 2.2 | CO, unknown | 98.4 |
| $NiO/MoO_3$ (Mo/Ni molar ratio = 2.2) | 83.8 | 1.7 | CO, unknown | 95.4 |

HCHO, % indicates the selectivity for HCHO. Likewise, DME, % indicates the selectivity for DME.

Example 3

Additional comparative conversion and selectivity data for oxidizing methanol to formaldehyde using varying catalysts at varying temperatures and the like is provided in Table 3 below.

TABLE 3

| Catalyst in Upstream Region | Surface Area of Upstream Catalyst | Material in Intermediate Region | Catalyst in Downstream Region | Temp ° C. | HCHO % | DME % | DMM % | CO % | $CO_2$ % | Unknown | Conversion % | Flow rate, sccm | Upstream Cat./ Downstream Cat., Weight Ratio |
|---|---|---|---|---|---|---|---|---|---|---|---|---|---|
| $NiMoO_4$ (0.0153 g) | 9.5 $m^2/g$ | Quartz Wool | n/a | 300 | 100 | 0 | 0 | 0 | 0 | 0 | 2.4 | 100 | n/a |
| $NiMoO_4$ (0.0153 g) | 9.5 $m^2/g$ | Quartz Wool | n/a | 380 | 87.4 | 2.6 | 0.8 | 0 | 0 | 9.2 | 25.5 | 100 | n/a |
| $NiMoO_4$ | 9.5 $m^2/g$ | Quartz | n/a | 450 | 78.6 | 0.6 | 0 | 9.2 | 2.7 | 8.9 | 76.3 | 100 | n/a |

TABLE 3-continued

| Catalyst in Upstream Region | Surface Area of Upstream Catalyst | Material in Intermediate Region | Catalyst in Downstream Region | Temp ° C. | HCHO % | DME % | DMM % | CO % | CO$_2$ % | Unknown | Conversion % | Flow rate, sccm | Upstream Cat./Downstream Cat., Weight Ratio |
|---|---|---|---|---|---|---|---|---|---|---|---|---|---|
| Perstorp (0.0153 g) | 7.8 m$^2$/g | Quartz Wool | n/a | 300 | 81.7 | 6.7 | 1.3 | 0 | 0 | 10.4 | 23.2 | 100 | n/a |
| Perstorp (0.0152 g) | 7.8 m$^2$/g | Quartz Wool | n/a | 380 | 88.0 | 1.6 | 0 | 0 | 0 | 10.3 | 74.6 | 100 | n/a |
| Perstorp (0.0152 g) | 7.8 m$^2$/g | Quartz Wool | n/a | 450 | 88.2 | 1.0 | 0.3 | 0 | 0 | 10.5 | 75.5 | 100 | n/a |
| NiMoO$_4$ (0.015 g) | 9.5 m$^2$/g | Quartz Wool | Perstorp (0.015 g) | 300 | 84.3 | 5.9 | 0.8 | 0 | 0 | 9.0 | 30.9 | 100 | 1.0 |
| NiMoO$_4$ (0.015 g) | 9.5 m$^2$/g | Quartz Wool | Perstorp (0.015 g) | 380 | 84.4 | 1.6 | 0 | 2.6 | 1.7 | 9.7 | 86.1 | 100 | 1.0 |
| NiMoO$_4$ (0.015 g) | 9.5 m$^2$/g | Quartz Wool | Perstorp (0.015 g) | 450 | 80.0 | 0.4 | 0 | 9.7 | 1.9 | 8.2 | 97.4 | 100 | 1.0 |
| NiMoO$_4$ (0.046 g) @ 350° C. | 9.5 m$^2$/g | Quartz Wool | Perstorp (0.0161 g) @ 300° C. | 350/300 | 66.7 | 1.6 | 0 | 15.0 | 9.1 | 7.6 | 92.3 | 51 | 2.86 |
| NiMoO$_4$ (0.0203 g) @ 380° C. | 9.5 m$^2$/g | Quartz Wool | Perstorp (0.0167 g) @ 300° C. | 380/300 | 79.3 | 1.2 | 0 | 7.5 | 2.8 | 9.1 | 78.0 | 100 | 1.21 |
| NiMoO$_4$ (0.0203 g) @ 380° C. | 9.5 m$^2$/g | Quartz Wool | Perstorp (0.0167 g) @ 320° C. | 380/320 | 77.6 | 0.8 | 0 | 9.9 | 2.7 | 9.0 | 88.4 | 100 | 1.21 |
| NiMoO$_4$ (0.0311 g) @ 360° C. | 9.5 m$^2$/g | Quartz Wool | Perstorp (0.0136 g) @ 320° C. | 360/320 | 86.2 | 3.4 | 0 | 0 | 0 | 10.4 | 46.2 | 100 | 2.30 |
| NiMoO$_4$ (0.0311 g) @ 360° C. | 9.5 m$^2$/g | Quartz Wool | Perstorp (0.0136 g) @ 350° C. | 360/350 | 86.7 | 2.8 | 0 | 0 | 0 | 10.5 | 62.6 | 100 | 2.30 |
| NiMoO$_4$ (0.0311 g) @ 360° C. | 9.5 m$^2$/g | Quartz Wool | Perstorp (0.0136 g) @ 360° C. | 360/360 | 87.6 | 2.3 | 0 | 0 | 0 | 10.2 | 69.4 | 100 | 2.30 |
| NiMoO$_4$ (0.0311 g) @ 377° C. | 9.5 m$^2$/g | Quartz Wool | Perstorp (0.0136 g) @ 320° C. | 377/320 | 82.2 | 1.3 | 0 | 5.1 | 2.1 | 9.2 | 72.1 | 100 | 2.30 |
| NiMoO$_4$ (0.0311 g) @ 377° C. | 9.5 m$^2$/g | Quartz Wool | Perstorp (0.0136 g) @ 350° C. | 377/350 | 82.0 | 1.3 | 0 | 4.7 | 2.0 | 10.0 | 79.1 | 100 | 2.30 |
| NiMoO$_4$ (0.0592 g) @ 363° C. | 9.5 m$^2$/g | Quartz Wool | Perstorp (0.0141 g) @ 320° C. | 363/320 | 82.3 | 1.5 | 0 | 4.8 | 1.9 | 9.4 | 80.1 | 100 | 4.20 |
| NiMoO$_4$ (0.0592 g) @ 363° C. | 9.5 m$^2$/g | Quartz Wool | Perstorp (0.0141 g) @ 350° C. | 363/350 | 83.0 | 1.3 | 0 | 4.5 | 1.8 | 9.4 | 86.3 | 100 | 4.20 |
| NiMoO$_4$ (0.0592 g) @ 363° C. | 9.5 m$^2$/g | Quartz Wool | Perstorp (0.0141 g) @ 360° C. | 363/360 | 83.7 | 1.4 | 0 | 3.6 | 1.7 | 9.5 | 85.4 | 100 | 4.20 |

Currently, flow rates below 100 sccm are not desirable. At lower flow rates, increased amounts of CO are produced. Perstorp is made by Perstorp AB of Perstorp, Sweden and sold by Perstorp Polyols of Toledo, Ohio under the product designation KH-26B.

We claim:

1. A process for oxidizing methanol to formaldehyde in a fixed bed reactor having an inlet end, an upstream region, a downstream region, and an outlet end, said process comprising the steps of:
   (a) introducing a reactant gas feed stream into said inlet end, wherein said reactant gas feed stream comprises methanol; and
   (b) flowing said reactant gas feed stream through said upstream region and oxidizing said methanol to said formaldehyde to yield a partially oxidized reactant gas feed stream containing formaldehyde and potentially unoxidized residual methanol;
   (c) and then flowing said partially oxidized reactant gas feed stream through said downstream region and oxidizing said residual methanol to formaldehyde to yield a product gas stream,
   wherein a first metal molybdate catalyst suitable for oxidizing said methanol to said formaldehyde is distributed in said upstream region, wherein said first metal molybdate catalyst is substantially free of volatile MoO$_3$, and wherein a second metal molybdate catalyst suitable for oxidizing any of said residual methanol to said formaldehyde is distributed in said downstream region.

2. The process of claim 1 further comprising selecting said first metal molybdate catalyst from the group consisting of molybdates of group IIB metals, molybdates of group IIIA metals, molybdates of group IVB metals, molybdates of group VIB metals, molybdates of group VIIB metals, molybdates of group VIII metals and mixtures thereof.

3. The process of claim 2 further comprising selecting said first metal molybdate catalyst from the group consisting of NiMoO$_4$, MnMoO$_4$, Cr$_2$(MoO$_4$)$_3$, ZnMoO$_4$, CoMoO$_4$, Al$_2$(MoO$_4$)$_3$, Zr(MoO$_4$)$_2$ and mixtures thereof.

4. The process of claim 3, wherein said second metal molybdate further comprises excess MoO$_3$.

5. The process of claim 1 further comprising selecting said second metal molybdate from the group consisting of $Fe_2(MoO_4)_3/MoO_3$, $CoMoO_4/MoO_3$, $NiMoO_4/MoO_3$, $Al_2(MoO_4)_3/MoO_3$, $Zr(MoO_4)_3/MoO_3$, $MnMoO_4/MoO_3$, $Cr_2(MoO_4)_3/MoO_3$ and mixtures thereof.

6. The process of claim 5, wherein said second metal molybdate is formed in situ from mixtures of $MoO_3$ and group VIII metal oxides.

7. The process of claim 1, wherein said reactant gas feed stream is introduced into said inlet end at a flow rate of at least about 0.1 $sec^{-1}$ space velocity.

8. The process of claim 1, wherein said formaldehyde in said product gas stream has a conversion of at least 85% and a selectivity of at least 90%.

9. The process of claim 1, wherein a weight ratio of said first metal molybdate to said second metal molybdate is at least about 1.

10. The process of claim 9, wherein said weight ratio is from about 1 to about 5 and wherein said first metal molybdate has a surface area of about 9.5 $m^2/g$ when said first metal molybdate is $NiMoO_4$.

11. The process of claim 1, wherein said upstream region comprises from about ¼ to about ½ of a total depth of said fixed bed reactor and said upstream region is nearest said inlet end.

12. The process of claim 1, wherein said downstream region comprises from about ¼ to about ¾ of a total depth of said fixed bed reactor and said downstream end is nearest said outlet end.

13. The process of claim 1, wherein said reactant gas feed stream comprises methanol, air and an optional inert carrier gas.

14. The process of claim 13, wherein said inert carrier gas is selected from the group consisting of $N_2$, He and mixtures thereof.

15. The process of claim 1, wherein said upstream region is maintained at an upstream reactor temperature range from about 300° C. to about 450° C. and said downstream region is maintained at a downstream reactor temperature from about 300° C. to about 450° C.

16. The process of claim 1, wherein said reactor is operated at a reactor pressure from about 7 psia to about 165 psia.

17. The process of claim 1, wherein said second metal molybdate is formed in situ from NiO and $MoO_3$.

18. The process of claim 1, wherein said second metal molybdate is formed in situ from $Fe_2O_3$ and $MoO_3$.

* * * * *